(12) United States Patent
Ebbutt et al.

(10) Patent No.: US 7,150,748 B2
(45) Date of Patent: Dec. 19, 2006

(54) BIPOLAR COAGULATING INSTRUMENT

(75) Inventors: Julian Mark Ebbutt, Cardiff (GB); Anthony Keith Atwell, Newport (GB)

(73) Assignee: Gyrus Medical Limited, Cardiff (GB)

( * ) Notice: Subject to any disclaimer, the term of this patent is extended or adjusted under 35 U.S.C. 154(b) by 192 days.

(21) Appl. No.: 10/924,953

(22) Filed: Aug. 25, 2004

(65) Prior Publication Data

US 2005/0283151 A1    Dec. 22, 2005

(30) Foreign Application Priority Data

Jun. 18, 2004    (GB)    ................................ 0413705.5

(51) Int. Cl.
*A61B 18/18*    (2006.01)
(52) U.S. Cl. ............................. 606/50; 606/45; 606/48; 606/49
(58) Field of Classification Search .................. 606/45, 606/48–50
See application file for complete search history.

(56) References Cited

U.S. PATENT DOCUMENTS

| 3,970,088 | A | * | 7/1976 | Morrison ...................... 606/48 |
| 4,161,950 | A | * | 7/1979 | Doss et al. .................... 606/48 |
| 4,202,337 | A | * | 5/1980 | Hren et al. .................... 606/48 |
| 4,850,353 | A |   | 7/1989 | Statz et al. |
| 4,862,890 | A | * | 9/1989 | Stasz et al. ................... 606/48 |
| 5,542,945 | A | * | 8/1996 | Fritzsch ........................ 606/48 |
| 5,611,798 | A |   | 3/1997 | Eggers et al. |
| 5,658,281 | A | * | 8/1997 | Heard .......................... 606/48 |
| 6,056,747 | A | * | 5/2000 | Saadat et al. ................. 606/50 |
| 2003/0130658 | A1 | * | 7/2003 | Goble et al. .................. 606/48 |
| 2004/0116923 | A1 | * | 6/2004 | Desinger ...................... 606/50 |
| 2005/0273097 | A1 | * | 12/2005 | Ryan .......................... 606/45 |

FOREIGN PATENT DOCUMENTS

| WO | WO 03/055402 | 7/2003 |
| WO | WO 03/088806 | 10/2003 |

OTHER PUBLICATIONS

Search Report for corresponding International Patent Application PCT/GB2005/002143, mailed Mar. 8, 3005.

* cited by examiner

*Primary Examiner*—Michael Peffley
*Assistant Examiner*—Alex Toy
(74) *Attorney, Agent, or Firm*—Nixon & Vanderhye P.C.

(57) ABSTRACT

A bipolar coagulating instrument includes a blade-like electrode assembly comprising an upper planar face and a lower planar face separated by an intermediate portion of insulating material therebetween. The upper face includes first and second electrodes separated by a first insulating member, and the lower face includes third and fourth electrodes separated by a second insulating member. The first and second insulating members are out of correlation one with respect to the other, such that there is at least one region in which the first electrode overlies the third electrode, and at least one other region in which the first electrode overlies the fourth electrode. A cutting electrode is provided between the upper and lower faces, extending marginally beyond the periphery thereof.

16 Claims, 2 Drawing Sheets

BIPOLAR COAGULATING INSTRUMENT

BACKGROUND OF THE INVENTION

This invention relates to a bipolar electrosurgical instrument such as a scalpel blade. Such instruments are commonly used for the coagulation and/or cutting of tissue in surgical intervention, most commonly in "keyhole" or minimally-invasive surgery, but also in "open" surgery.

Electrosurgical devices generally fall into two categories, monopolar and bipolar. In a monopolar device, a radio frequency signal is supplied to an active electrode which is used to treat tissue at a target site, an electrical circuit being completed by a grounding pad which is generally a large area pad attached to the patient at a location remote from the target site. In contrast, in a bipolar arrangement, both an active and a return electrode are present on the instrument, and the current flows from the active electrode to the return electrode. The present invention relates to a bipolar device.

In minimally-invasive surgery, it is essential to be able to coagulate tissue in order to stem or prevent bleeding. By definition, the procedure is taking place in a confined space, and it is often difficult or inconvenient to have to re-orient the surgical instrument repeatedly in order to achieve such coagulation. The present invention provides a surgical instrument capable of the coagulation of tissue, the instrument providing a plurality of regions in which coagulation can be performed.

BRIEF DESCRIPTION OF THE INVENTION

Accordingly there is provided a bipolar coagulating instrument including a blade-like electrode assembly comprising an upper planar face and a lower planar face separated by an intermediate layer of insulating material therebetween, the upper face including first and second electrodes separated by a first insulating member, and the lower face including third and fourth electrodes separated by a second insulating member, the first and second insulating members being out of correlation one with respect to the other, such that there is at least one region in which the first electrode overlies the third electrode, and at least one other region in which the first electrode overlies the fourth electrode.

By the term "blade-like" there is meant an instrument in which the thickness of the electrode assembly is considerably less than its width. Typically, the thickness of the electrode assembly is less than 5 mm, and preferably less than 3 mm. The aspect ratio of the electrode assembly is at least 1.5, that is to say the electrode assembly is at least 1.5 times as wide as it is thick. Preferably, the aspect ratio is at least 2.

By providing the at least one other region in which the first electrode overlies the fourth electrode, the instrument offers the user three different regions on the electrode assembly from which coagulation can be performed. Firstly, coagulation can be performed using the upper planar face, the coagulating current flowing between the first and second electrodes. Secondly, coagulation can be performed using the lower planar face, the coagulating current flowing between the third and fourth electrodes. Finally, coagulation can be performed between the upper and lower faces of the electrode assembly, the coagulating current flowing between the first and fourth electrodes, in the region in which they overlie one another.

In one convenient arrangement the first electrode is in electrical communication with the third electrode. Typically, the first electrode is integral with the third electrode. Similarly, the second electrode is conveniently in electrical communication with the fourth electrode, and is typically integral therewith.

Preferably, the at least one other region is adjacent to an edge of the blade-like electrode assembly, and conveniently adjacent to the tip thereof. In this way, the third region from which coagulation can be performed comprises the tip of the electrode assembly.

There are a number of ways in which the first and fourth electrodes can be made to overlie one another in the at least one region. In one arrangement the first and second insulating members are longitudinally-extending members, one being disposed at an angle to the other. Alternatively or additionally, the first and second insulating members are of a different shape one to the other. In yet another alternative arrangement, the first and second insulating members are of a similar shape, but located in a different orientation one to the other. One example of this is to have the first and second insulating members each comprise two sections disposed at an acute angle one to the other. Whichever arrangement is employed, it is essential that the first insulating member on the upper face of the electrode assembly is in some way out of correlation with the second insulating member on the lower face of the electrode assembly, so as to ensure that there is at least one region in which the electrodes on the upper face do not correspond with those on the lower face.

Typically, either the first insulating member or the second insulating member is integral with the intermediate layer of insulating material. Conceivably, both the first and second insulating members are integral with the intermediate layer.

In a preferred arrangement, there is additionally provided a cutting electrode, the cutting electrode being insulated from each of the first to fourth electrodes. In this way the instrument can be used to both cut and coagulate tissue, typically in a procedure such as a laparoscopic supracervical hysterectomy (LSH). Conveniently, the cutting electrode is located between the upper planar face and the lower planar face. Typically, the intermediate layer of insulating material is two parts, and the cutting electrode is located therebetween. Preferably, the cutting electrode protrudes from an edge of the blade-like electrode assembly. Thus, the edge of the electrode assembly can be used to cut tissue, and coagulation can be performed in any of the regions of the instrument as previously described. In this way, both cutting and coagulation can be performed with only minimal movement and re-orientation of the instrument being necessary, as is required in a minimally-invasive procedure.

BRIEF DESCRIPTION OF THE DRAWINGS

The invention will now be described, by way of example only, with reference to the accompanying drawings, in which.

DETAILED DESCRIPTION OF THE INVENTION

Figure 1:
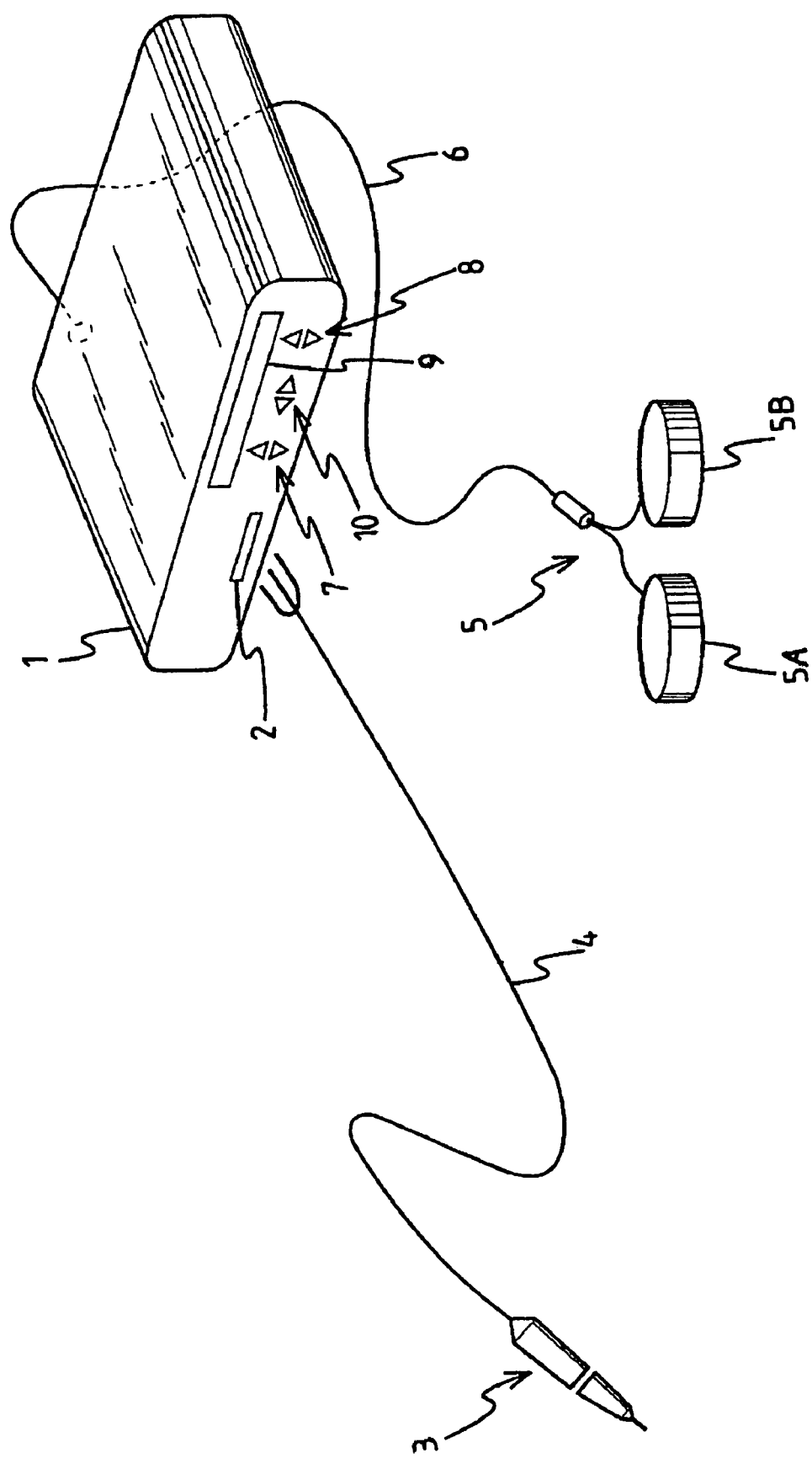
FIG. 1 is a schematic diagram of an electrosurgical system including an electrosurgical instrument constructed in accordance with the present invention.

Referring to FIG. 1, a generator 1 has an output socket 2 providing a radio frequency (RF) output for an instrument 3 via a connection cord 4. Activation of the generator 1 may be performed from the instrument 3 via a connection in the cord 4, or by means of a footswitch unit 5, as shown, connected to the rear of the generator by a footswitch connection cord 6. In the illustrated embodiment, the footswitch unit 5 has two footswitches 5A and 5B for selecting a coagulation mode and a cutting mode of the generator 1 respectively. The generator front panel has push buttons 7 and 8 for respectively setting coagulation and cutting power levels, which are indicated in a display 9. Push buttons 10 are provided as an alternative means for selection between coagulation and cutting modes.

Figure 2:
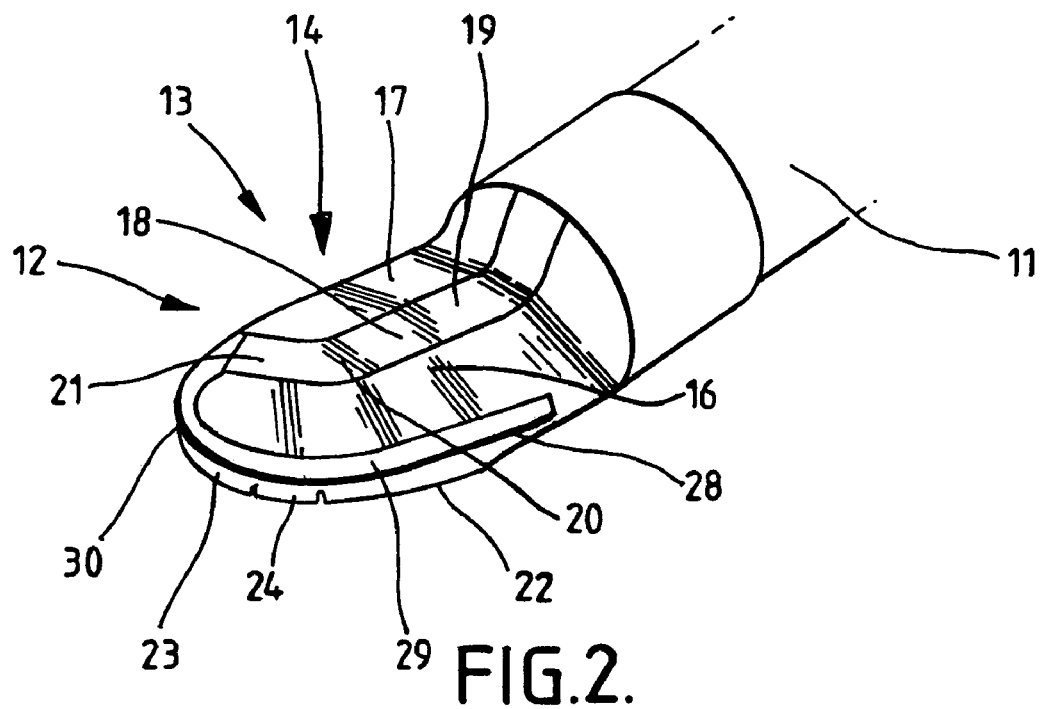
FIG. 2 is a schematic perspective view of an electrosurgical instrument constructed in accordance with the present invention.
Figure 3:
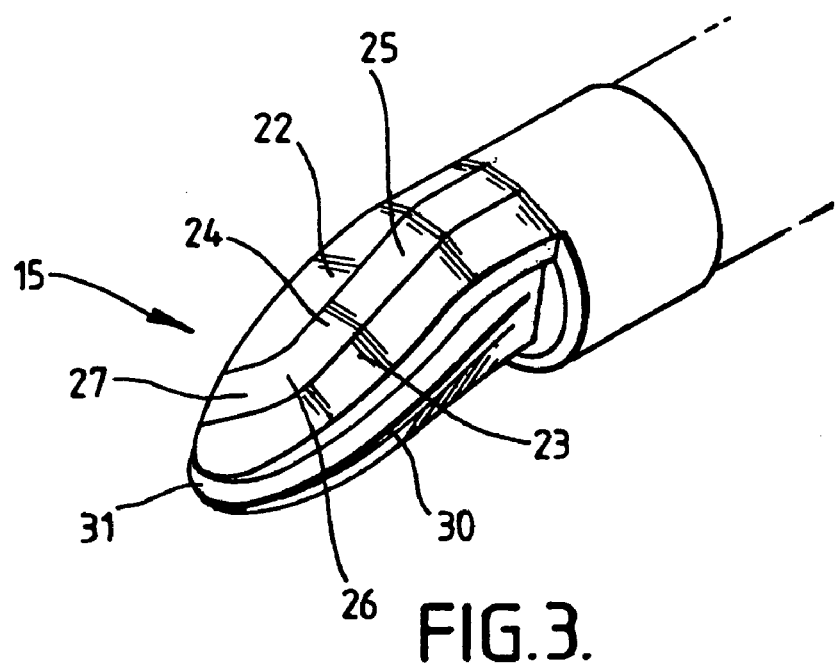
FIG. 3 is a schematic perspective view of the instrument of FIG. 2, shown from underneath.

Referring to FIGS. 2 and 3, the instrument 3 is shown having a longitudinally-extending shaft 11 and a blade-like electrode assembly 12. The electrode assembly 12 is in the form of a spatula 13, inclined at an angle of approx 20 degrees to the axis of the shaft 11, and having a broad upper face 14, a broad lower face 15, and a relatively thin cross-section. The upper face 14 is constituted by a first electrode 16 (designated the upper left electrode), and a second electrode 17 (designated the upper right electrode). The first and second electrodes 16 and 17 are formed of copper, plated with hard gold over nickel.

Between the first and second electrodes 16 and 17 is a first insulating member 18, formed of ceramic. The first insulating member 18 has a "dog-leg" shape, with a longitudinally-extending stem 19, an elbow portion 20, and an end portion 21 extending at an angle of approx 45 degrees. The end portion 21 is angled towards the second electrode 17, so that the first electrode 16 is of a larger surface area than the second electrode.

The lower face 15 is constituted by a third electrode 22 (designated the lower left electrode), and a fourth electrode 23 (designated the lower right electrode), again formed of copper plated as before. Between the third and fourth electrodes 22 and 23 is a second insulating member 24, again formed of ceramic. The second insulating member 24 also has a "dog-leg" shape, with a longitudinally-extending stem 25, an elbow portion 26, and an end portion 27. The end portion 27 is similarly angled at approx 45 degrees, but in the opposite orientation to that of the first insulating member 18, such that the fourth electrode 23 has a larger surface area than the third electrode 22. Along one side of the electrode assembly 12, the first electrode 16 overlies the third electrode 22. Along the opposite side of the electrode assembly 12, the second electrode 17 overlies the fourth electrode 23. However, the different orientation of the first and second insulating members 18 and 24 means that, towards the tip of the electrode assembly 12, the first electrode 16 overlies the fourth electrode 23. This is significant, as will be explained in further detail later.

Between the upper face 14 and the lower face 15 is an intermediate portion 28, comprising a three-layer structure consisting of an upper ceramic layer 29, a planar cutting electrode 30, and a lower ceramic layer 31. The upper and lower ceramic layers 29 and 31 serve to insulate the cutting electrode 30 from the first to fourth electrodes 16, 17, 22 and 23 previously described. The cutting electrode 30 is formed of stainless steel, and extends marginally beyond the periphery of the remainder of the electrode assembly 12.

The first and third electrodes 16 and 22 (the upper and lower left hand electrodes) are formed from a unitary metallic member, and are connected via a lead (not shown) to one output of the electrosurgical generator 1. Similarly, the second and fourth electrodes 17 and 23 (the upper and lower right hand electrodes) are also formed from a unitary metallic member, and are connected via a lead (not shown) to another output of the generator 1. The cutting electrode 30 is also connected via a lead (not shown) to an output of the generator 1. The generator 1 has a switchable output, as described in our co-pending European patent application EP 1287788.

The operation of the instrument 3 will now be described. The instrument 3 is introduced into the body of the patient though a surgical trocar (not shown). When the surgeon wishes to use the instrument 3 to cut tissue, the footswitch 5B is depressed sending an electrosurgical cutting signal to the instrument. This cutting signal is supplied to the cutting electrode 30, with the first to fourth electrodes 16, 17, 22 and 23 being commonly connected and acting as the return electrode for the cutting operation. This electrosurgical cutting is described in more detail in our co-pending PCT patent application WO03/055402.

When the surgeon wishes to coagulate tissue, the footswitch 5A is depressed sending a coagulating signal to the instrument 3. This coagulating signal is supplied between the left hand electrodes 16 and 22 on the one hand, and the right hand electrodes 17 and 23 on the other hand. This gives the surgeon three different options for coagulation. Firstly, the surgeon can use the upper face of the electrode assembly 12, coagulating tissue between the first and second electrodes 16 and 17 across the first insulating member 18. Secondly, the surgeon can use the lower face of the electrode assembly 12, coagulating tissue between the third and fourth electrodes 22 and 23 across the second insulating member 24. Finally, the surgeon can use the tip of the electrode assembly 12, coagulating tissue between the first and fourth electrodes 16 and 23 across the intermediate portion 28. This is only possible given the different orientations of the first and second insulating members 18 and 24, allowing the first and fourth electrodes 16 and 23 to overlie one another in the tip region of the electrode assembly 12. Thus, the surgeon can coagulate tissue using three different parts of the electrode assembly 12, thereby minimising the need for the movement and re-orientation of the instrument 3. Furthermore, the use of the upper and lower faces 15 and 15 of the instrument 3 is suitable for large area coagulation, while the use of the tip region of the instrument is more suitable for point coagulation. The three different parts of the electrode assembly 12 used for coagulation can, of course, be used in combination. For example, the tip coagulation described above can be enhanced by a contribution from coagulation between the first and second, and/or third and fourth electrodes 16, 17, 22 and 23. This provides a larger coagulation area when using the tip area, if desired.

It will be appreciated that other designs and shapes of the insulation members 18 and 24 are possible, while still giving at least one area in which the first electrode 16 overlies the fourth electrode 23. For example, the first and second insulation members 18 and 24 may be substantially identical, and yet extend at different angles with respect to the longitudinal axis of the shaft 11. Alternatively, the insulation members 18 and 24 may each have a different shape. Whichever design is employed, the non-correlation between the insulation members 18 and 24 serves to provide the additional coagulation area in which the first electrode 16 overlies the fourth electrode 23.

Although the present invention has been described in terms of a particular embodiment, it is not intended that the invention be limited to that embodiment. Modifications of the embodiment within the spirit of the invention will be apparent to those skilled in the art. The scope of the invention is defined by the claims that follow.

What is claimed is:

1. A bipolar coagulating instrument including a blade-like electrode assembly comprising an upper planar face and a lower planar face separated by an intermediate layer of insulating material therebetween, the upper face including first and second electrodes separated by a first insulating member and between which coagulation can be performed, and the lower face including third and fourth electrodes separated by a second insulating member and between which coagulation can be performed, the first and second insulating members being out of correlation one with respect to the other, such that there is at least one region in which the first electrode overlies the third electrode, and at least one other region in which the first electrode also overlies the fourth electrode, whereby coagulation can be performed between the first and fourth electrodes.

2. A bipolar coagulating instrument according to claim 1, wherein the first electrode is in electrical communication with the third electrode.

3. A bipolar coagulating instrument according to claim 2, wherein the first electrode and the third electrode are formed from a unitary metallic member.

4. A bipolar coagulating instrument according claim 1, wherein the second electrode is in electrical communication with the fourth electrode.

5. A bipolar coagulating instrument according to claim 4, wherein the second electrode and the fourth electrode are formed from a unitary metallic member.

6. A bipolar coagulating instrument according to claim 1, wherein the at least one other region is adjacent to an edge of the blade-like electrode assembly.

7. A bipolar coagulating instrument according to claim 6, wherein the at least one other region is adjacent to the tip of the blade-like electrode assembly.

8. A bipolar coagulating instrument according to claim 1, wherein the first and second insulating members are longitudinally-extending members, one being disposed at an angle to the other.

9. A bipolar coagulating instrument according to claim 1, wherein the first and second insulating members are of a similar shape, but located in a different orientation one to the other.

10. A bipolar coagulating instrument according to claim 9, wherein the first and second insulating members each comprise two sections disposed at an acute angle one to the other.

11. A bipolar coagulating instrument according to claim 1, wherein the first insulating member is integral with the intermediate layer of insulating material.

12. A bipolar coagulating instrument according to claim 1, wherein the second insulating member is integral with the intermediate layer of insulating material.

13. A bipolar coagulating instrument according to claim 1, further comprising a cutting electrode, the cutting electrode being insulated from each of the first to fourth electrodes.

14. A bipolar coagulating instrument according to claim 13, wherein the cutting electrode is located between the upper planar face and the lower planar face.

15. A bipolar coagulating instrument according to claim 14, wherein the intermediate layer of insulating material is of two parts, and the cutting electrode is located therebetween.

16. A bipolar coagulating instrument according to claim 13, wherein the cutting electrode protrudes from an edge of the blade-like electrode assembly.

* * * * *